United States Patent [19]
Belle et al.

[11] Patent Number: 6,083,507
[45] Date of Patent: Jul. 4, 2000

[54] COMPOSITION FOR ELIMINATING THE BUILDUP OF HARMFUL TOXINS AND IMPROVING ENERGY, MENTAL CLARITY AND WASTE ELIMINATION

[76] Inventors: Maria Belle, 20247 Hacienda Ct., Boca Raton, Fla. 33427; Mark Scheinberg, 4961 NW. 55th St., Coconut Creek, Fla. 33073

[21] Appl. No.: 09/033,423

[22] Filed: Mar. 2, 1998

[51] Int. Cl.[7] ................................................. A01N 65/00
[52] U.S. Cl. ......................................................... 424/195.1
[58] Field of Search ...................... 424/195.1; 435/195.1

[56] References Cited

U.S. PATENT DOCUMENTS

| | | | |
|---|---|---|---|
| 5,266,318 | 11/1993 | Taylor-McCord | 424/195.1 |
| 5,332,579 | 7/1994 | Umbdenstock et al. | 424/195.1 |
| 5,614,224 | 3/1997 | Womack | 424/646 |
| 5,730,988 | 3/1998 | Womack | 424/195.1 |

OTHER PUBLICATIONS

Commerical Product "Wounded Warrior" sold by Mast General Store since 1991 Internet Web Site http:/www.highsouth.com/remote/mastgeneralstore, 1991.

Commerical Product "Neuro Clear" Gotu Kola sold by BioSynergy Health Alternatives Internet Web Site http://www.biosynergy.com/bios.htm, 1999.

*Primary Examiner*—Herbert J. Lilling
*Attorney, Agent, or Firm*—Scott L. Lampert

[57] ABSTRACT

A composition for the elimination of hasmifl toxin buildup comprising quantities of gotu-kola, whole leaf aloe-vera, lactobacilli organism and folic acid.

2 Claims, No Drawings

COMPOSITION FOR ELIMINATING THE BUILDUP OF HARMFUL TOXINS AND IMPROVING ENERGY, MENTAL CLARITY AND WASTE ELIMINATION

BACKGROUND OF THE INVENTION

1. Field of the Invention

The present invention relates to ingestible nutritional compositions for the elimination of harmful toxin buildup in the body and, more particularly, to an herbal composition that cleanses internal organs and improves energy, mental clarity and the elimination of waste.

2. Description of the Related Art

The use of herbs and plants to treat ailments and generally improve overall health has become commonplace. Aloe vera and gotu kola are herbs and plants commonly used for such purposes. The benefits of both aloe vera and gotu kola are well documented.

Gotu kola is an herb which is believed to have been used over a thousand years ago in India and China. Healers in India used gotu kola to treat skin inflammations and as a mild diuretic and in China to treat emotional disorders, such as depression, that may be caused by physical problems. It has also been used to reduce fevers, to relieve congestion due to colds and upper respiratory infections and as a nerve tonic to promote relaxation and to enhance memory.

Recent studies have shown that gotu kola may have a positive effect on the circulatory system by strengthening the veins and capillaries, thereby improving the flow of blood throughout the body. As such, it has been reported that it has been successfully used to treat phlebitis, leg cramps, leg swelling and other circulatory related problems in the legs. It is believed that its beneficial effect on circulation may help improve memory and brain function.

Applied externally or taken by mouth, aloe vera has been found to be effective in treating countless minor ailments. Based on studies of the gel found inside the aloe vera leaf, it is believed that aloe vera contains more than seventy essential ingredients including many vitamins, minerals, enzymes, protein and amino acids. Applied externally, aloe vera is known to act as a type of "wound hormone" that accelerates the rate of healing of injured surfaces and is typically used to treat ailments, such as, burns, psoriasis, eczema, acne, stings, scrapes, abrasions, bruises, sore muscles, cold sores, sprains, arthritis, etc. Taken internally, aloe vera is believed to be effective in treating such ailments as insomnia, infection, indigestion, heartburn, constipation, ulcers, arthritis, etc.

Constipation, or the infrequent and difficult passage or elimination of stool, is a common problem. Millions of people, including both children and adults, suffer from this condition. Although it is generally not a serious condition, it may be extremely bothersome and may, in fact, be a symptom of a more serious underlying disorder. Furthermore, if not treated properly, constipation may lead to other complications, such as hemorrhoids or fissures.

In addition to the use of aloe vera, there are several different treatments currently used to treat constipation. For many people, it is believed that dietary and lifestyle improvements can lessen the chances of constipation. For others, simply improving bowel habits, i.e., not ignoring the urge to have a bowel movement, can lessen the chances of constipation. Laxatives are also widely used for the treatment of constipation.

Both aloe vera and gotu kola are commonly used, by themselves, for the treatment of the ailments discussed above. Furthermore, several compositions utilize either aloe vera or gotu kola, in combination with other elements, to treat particular ailments. For instance, U.S. Pat. No. 5,614,224 discloses a nutritional supplement for diabetics which may include herbs, such as gotu kola, which may be beneficial in treating the causes or symptoms of diabetes. Similarly, U.S. Pat. No. 5,332,579 discloses a nutritional supplement for optimizing cellular health which may include herbs, such as gotu kola. Also, U.S. Pat. No. 5,266,318 discloses a skin therapeutic mixture containing aloe vera.

Although aloe vera, gotu kola and their prior art compositions are useful for their intended purposes, none has proven to be entirely effective. Specifically, the effectiveness of aloe vera in treating constipation has not been great and, consequently, has not been a preferred method of doing so. Furthermore, the other treatments of constipation discussed above have also not proven to be entirely effective. The ability to make diet and lifestyle changes often requires great sacrifice and is extremely difficult for many people. Similarly, people with poor bowel habits typically have such poor habits because of other personality or character traits. It is not uncommon for people who are busy at work or who have many things to do to ignore the urge to have a bowel movement until they have completed what they are doing. Such habits are difficult to break and it may be unreasonable to expect them to be broken. Lastly, the use of laxatives often pose problems due to misuse and overuse. There are several types of laxatives which work in different ways. It is not uncommon for a person to purchase the wrong laxative or use it improperly. Also, many laxative users become dependant upon them and continually increase the dosage until the intestine becomes insensitive and the laxative no longer performs its intended function.

Furthermore, there is presently no known composition which includes both aloe vera and gotu kola or other herbs or plants which effectively provides the combination of benefits associated with each individually. Specifically, there is presently no known ingestible herbal composition which effectively eliminates harmful toxin buildup in the body, cleanses internal organs and improves energy, mental clarity and the elimination of waste.

Accordingly, there is still a need in the art for an ingestible herbal composition which effectively eliminates harmful toxin buildup in the body, cleanses internal organs and improves energy, mental clarity and the elimination of waste. The present invention is particularly suited to overcome those problems which remain in the art in a manner not previously known. Not only does the composition of the present invention effectively provide the combination of benefits associated with aloe vera and gotu kola individually, but in combining aloe vera with gotu kola, the beneficial effects previously associated with each individually have been found to be enhanced. Specifically, it is believed that the composition of the present invention improves energy, mental clarity and the elimination of waste in a manner not previously accomplished by aloe vera or gotu kola individually.

SUMMARY OF THE INVENTION

The present invention is directed towards a new and improved ingestible composition for the elimination of harmful toxin buildup and the improvement of energy, mental clarity and the elimination of waste. The composition includes gotu-kola in combination with whole leaf aloe vera.

It is an object of the present invention to provide a new and improved ingestible composition for the elimination of harmful toxin buildup.

It is another object of the present invention to provide an ingestible composition which improves the digestive process.

It is also an object of the present invention to provide an ingestible composition which promotes healing of internal organs.

It is a further object of the present invention to provide an ingestible composition which improves the moisture content of the intestine walls and, accordingly, the elimination of waste.

It is yet another object of the present invention to provide an ingestible composition which improves a person's energy, mental clarity and general well-being.

It is yet a further object of the present invention to provide an ingestible composition which comprises only natural ingredients.

These and other objects and advantages of the present invention will become more readily apparent in the description which follows.

DETAILED DESCRIPTION OF THE PREFERRED EMBODIMENT

The present invention is directed towards a new and improved ingestible composition for the elimination of harmful toxin buildup and the improvement of energy, mental clarity and the elimination of waste. The composition includes gotu-kola in combination with aloe vera. The aloe vera is preferably whole leaf, but may be of any other suitable type.

The preferred embodiment of the present invention is in pill form and has the following composition:

| | |
|---|---|
| Gotu-Kola | 225 mg. |
| Aloe-Vera (Whole Leaf) | 225 mg. |

The form and specific composition of the present invention may be modified to accommodate different treatments. Specifically, the composition may include any suitable dosage of gotu-kola between 100 mg. and 2,000 mg. and aloe vera between 100 mg. and 2,000 mg.

The recommended dosage of the preferred embodiment for treatment is one to four tablets daily at bedtime with eight ounces of water. The specific dosage may be modified to accommodate the particular user.

Beginning users of the preferred embodiment of the present invention may encounter gas cramps caused by indigestive food being broken down and acted upon by bacteria. Such cramps may occur in beginning users, if at all, for the first few weeks. Accordingly, to combat such cramps, an alternative embodiment of the present invention includes 1 million to 10 billion organisms of a lactobacilli organism, such as acidophilus or a soil based organism, in combination with gotu kola and aloe vera. Lactobacilli organisms are widely known as a non-gas producing bacteria which improves intestinal function.

Additionally, the present invention may include 100 to 500 micrograms of folic acid in combination with gotu kola and aloe vera or in combination with gotu kola, aloe vera and a lactobacilli organism. In this alternative embodiment, folic acid acts as a catalyst to facilitate the chemical reaction in cells.

Various changes may be made within the spirit and scope of the invention as described above.

What is claimed is:

1. An ingestible composition which eliminates harmful toxin buildup, cleanses internal organs and improves energy, mental clarity and the elimination of waste comprising:

quantities of gotu-kola, wherein a dose of said gotu-kola ranges from 100 mg. to 2,000 mg., quantities of aloe-vera, wherein a dose of said aloe vera ranges from 100 mg. to 2,000 mg., quantities of lactobacilli organism, wherein a dose of said lactobacilli organism ranges from 1 million organisms to 10 billion organisms and quantities of folic acid, wherein a dose of said folic acid ranges from 100 micrograms to 500 micrograms.

2. An ingestible composition which eliminates harmful toxin buildup, cleanses internal organs and improves energy, mental clarity and the elimination of waste comprising:

quantities of gotu-kola, wherein a dose of said gotu-kola ranges from 100 mg. to 2,000 mg., quantities of aloe vera, wherein a dose of said aloe vera ranges from 100 mg. to 2,000 mg., and quantities of lactobacilli organism, wherein a dose of said lactobacilli organism ranges from 1 million organisms to 10 billion organisms.

* * * * *